United States Patent [19]
Jackson et al.

[11] Patent Number: 5,628,775
[45] Date of Patent: May 13, 1997

[54] FLEXIBLE BOND FOR SLEEVES ENCLOSING A BENDABLE ELECTRODE TIP ASSEMBLY

[75] Inventors: Jerome Jackson, Sunnyvale; Alan L. Kaganov, Palo Alto, both of Calif.

[73] Assignee: EP Technologies, Inc., Sunnyvale, Calif.

[21] Appl. No.: 603,503

[22] Filed: Feb. 20, 1996

Related U.S. Application Data

[63] Continuation of Ser. No. 515,473, Aug. 15, 1995, abandoned, which is a continuation of Ser. No. 402,732, Mar. 13, 1995, abandoned, which is a continuation of Ser. No. 260,484, Jun. 15, 1994, abandoned, which is a continuation of Ser. No. 143,985, Oct. 27, 1993, abandoned, which is a continuation of Ser. No. 823,204, Jan. 21, 1992, abandoned, which is a continuation-in-part of Ser. No. 790,206, Nov. 8, 1991, Pat. No. 5,257,451.

[51] Int. Cl.⁶ ............................................. A61N 1/02
[52] U.S. Cl. ............................................. 607/116; 607/119
[58] Field of Search ....................... 607/116, 119, 607/122, 123, 125–128; 128/642; 439/730, 932; 174/29, 131 R, DIG. 8

[56] References Cited

U.S. PATENT DOCUMENTS

| | | | |
|---|---|---|---|
| 4,711,027 | 12/1987 | Harris | 128/785 X |
| 4,885,432 | 12/1989 | Amoyal et al. | 174/DIG. 8 |
| 4,951,687 | 8/1990 | Ufford et al. | 128/786 |

FOREIGN PATENT DOCUMENTS

| | | | |
|---|---|---|---|
| 979833 | 1/1965 | United Kingdom | 174/DIG. 8 |

Primary Examiner—Jeffrey R. Jastrzab
Attorney, Agent, or Firm—Ryan, Maki, Mann & Hohenfeldt

[57] ABSTRACT

A flexible bond is formed between the exterior sleeve of a catheter guide tube and the exterior sleeve of the steerable electrode tip of the catheter. The flexible bond holds the sleeves in fluid tight abutment during twisting of the guide tube and bending of the electrode tip.

14 Claims, 10 Drawing Sheets

FLEXIBLE BOND FOR SLEEVES ENCLOSING A BENDABLE ELECTRODE TIP ASSEMBLY

This is a continuation Ser. No. 08/515,473 filed on Aug. 15, 1995 now abandoned; which is a Continuation of Ser. No. 08/402,732 filed on Mar. 13, 1995 now abandoned; which is a continuation of Ser. No. 08/260,484 filed on Jun. 15, 1994 now abandoned; which is a continuation of Ser. No. 08/143,985 filed on Oct. 27, 1993 now abandoned; which is a continuation of Ser. No. 07/823,204 filed on Jan. 21, 1992 now abandoned; which is a continuation-in-part of Ser. No. 07/790,206 filed Nov. 8 1991 (U.S. Pat. No. 5,257,451).

FIELD OF THE INVENTION

The invention generally relates to catheters. In a more specific sense, the invention relates to catheters that can be steered and manipulated within interior regions of the body from a location outside the body.

BACKGROUND OF THE INVENTION

Physicians make widespread use of catheters today in medical procedures to gain access into interior regions of the body. In its important that the physician can control carefully and precisely the movement of the catheter within the body.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery (which is typically the femoral arterial) into the interior region of the heart that is to be treated. The physician then further manipulates a steering mechanism to place the electrode carried on the tip of the catheter into direct contact with the tissue that is to be ablated. The physician directs radio frequency energy into the electrode tip to ablate the tissue and form a lesion.

Cardiac ablation especially requires the ability to precisely bend and shape the tip end of the catheter to position the ablation electrode.

SUMMARY OF THE INVENTION

The invention provides a flexible bond between the exterior sleeves associated with a guide tube and bendable electrode tip on a catheter. The bond is flexible enough to accommodate the bending movement between the electrode tip and the guide tube. Still, the bond provides added strength and resistance against wear and tear during repeated bending operations. The bond maintains the exterior sleeves in fluid tight abutment despite repeated bending of the electrode tip.

More particularly, the electrode tip assembly has a center support wire that is bendable in response to external forces. A guide tube is joined to an end of the center support wire for positioning the center support wire and for holding the center support wire while it bends in response to external forces.

A first exterior sleeve encloses the center support wire and has an end portion overlying the interior sleeve. The first exterior sleeve is sufficient flexible to conform to the shape of the center support wire while it bends.

A second exterior sleeve encloses the guide tube and has an end portion that extends beyond the second element and overlies the interior sleeve. The end portions of the first and second exterior sleeves abut about the interior sleeve. The second exterior sleeve serves to transmit twisting forces along the guide tube toward the center support wire.

According to the invention, an interior sleeve is attached to a portion of the center support wire near its junction with the guide tube. The abutting ends of the exterior sleeves overlie the interior sleeve. The interior sleeve has a tensile strength greater than the tensile strength of the first and second exterior sleeves.

Also according to the invention, a flexible adhesive bond is formed between the interior sleeve and the abutting overlying end portions of the first and second exterior sleeves. The flexible bond holds the end portions in abutment during twisting of the guide tube and bending of the central support wire.

DESCRIPTION OF THE PREFERRED EMBODIMENTS

Figure 1:
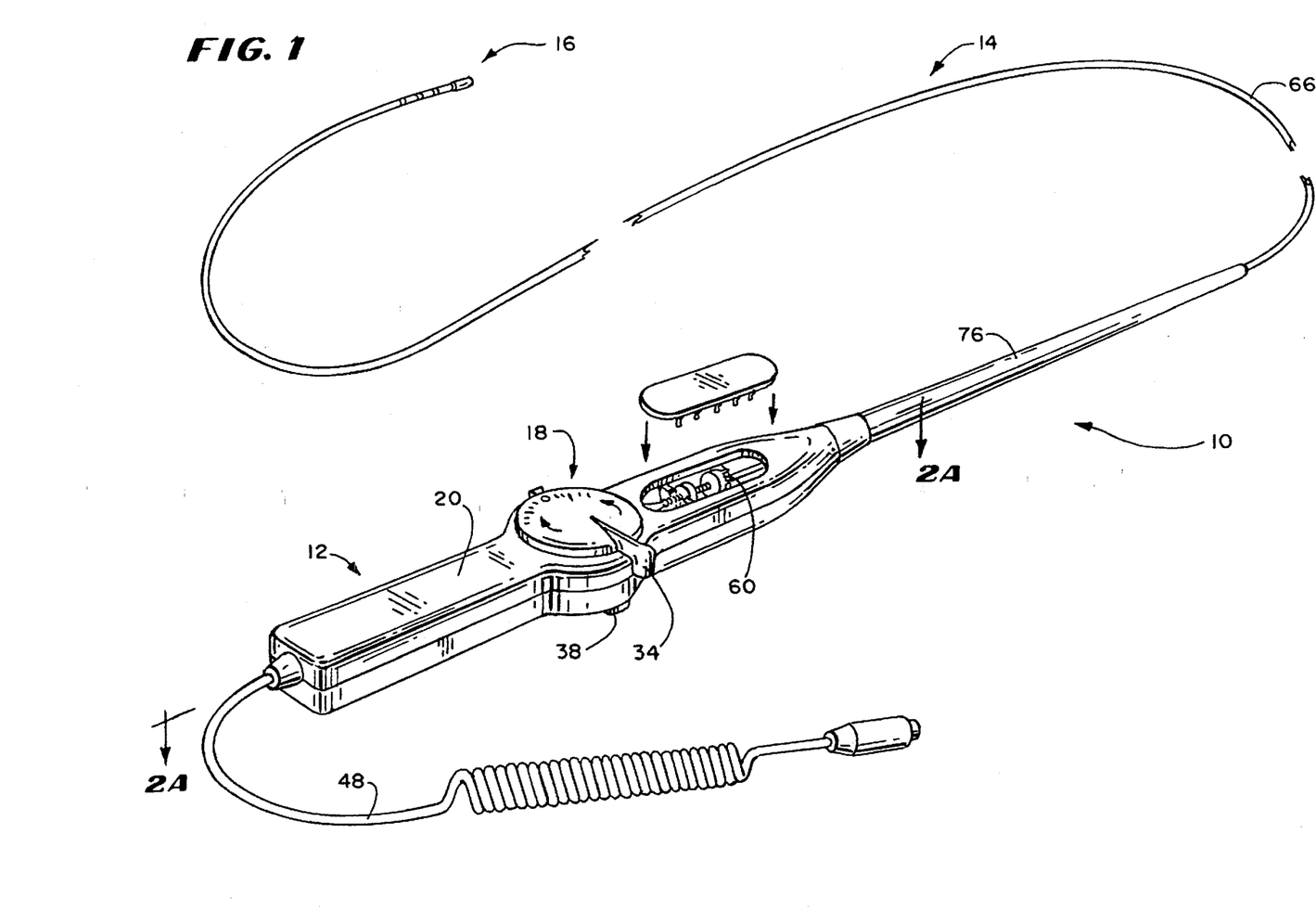
FIG. 1 is a perspective view of a catheter that embodies the features of the invention.

FIG. 1 shows the assembly of a steerable catheter 10 that embodies the features of the invention. As there shown, the catheter 10 includes three main parts or assemblies: the handle assembly 12, the guide tube assembly 14, and the electrode tip assembly 16.

The catheter 10 can be used in many different environments. This specification will describe the catheter 10 as used to provide electrophysiologic therapy in the interior regions of the heart.

When used for this purpose, a physician grips the handle assembly 12 to steer the guide tube assembly 14 through a main vein or artery (which is typically the femoral arterial) into the interior region of the heart that is to be treated. The physician then further manipulates a steering mechanism 18 on the handle assembly 12 (which will be described later) to place the electrode tip assembly 16 in contact with the tissue that is to be ablated. The physician directs radio frequency energy into the electrode tip assembly 16 to ablate the tissue contacting the electrode tip assembly 16.

Figure 2A:
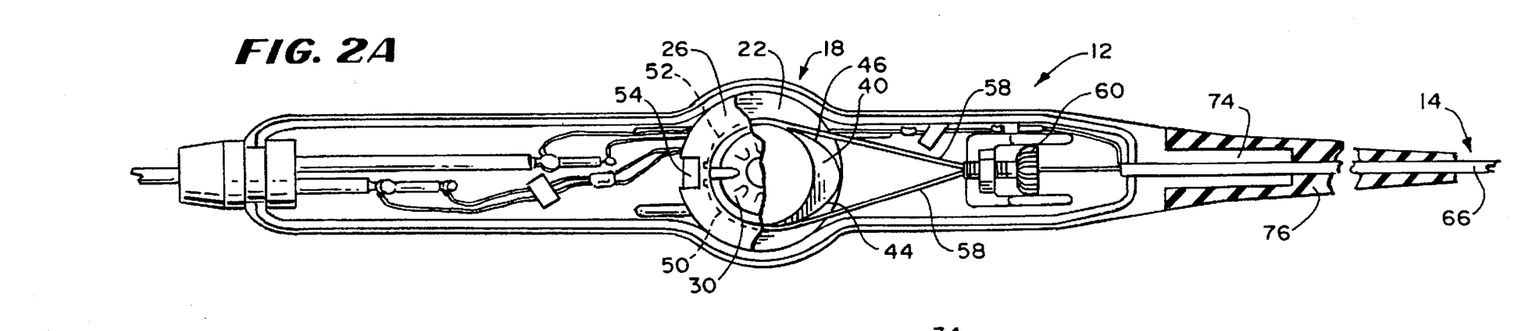
FIG. 2A is a side section view of the catheter taken generally along line 2A—2A in FIG. 1.
Figure 2B:
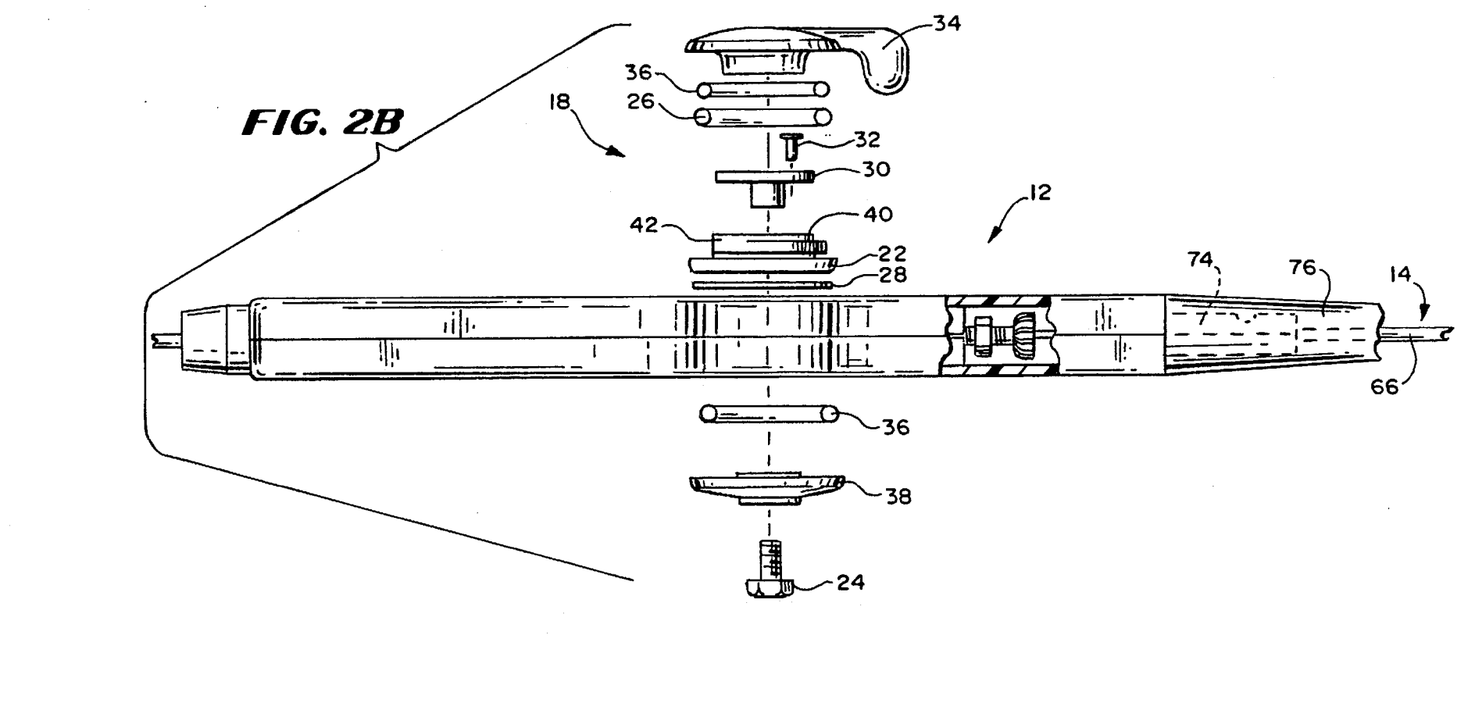
FIG. 2B is an exploded view of FIG. 2A.

As FIGS. 2A and 2B best show, the handle assembly 12 includes a housing 20 that encloses the steering mechanism 18. The steering mechanism 18 includes a rotating cam wheel 22 carried on a screw 24 within the housing 20. The cam wheel 22 is seated for rotation between a top washer 26 and a bottom washer 28. A lock nut 30 and a pin 32 couple an external steering lever to the top of the cam wheel 22. The steering lever 34 seats against an 0-ring 36.

Movement of the steering lever 34 by the user rotates the cam wheel 22 about the screw 24 within the housing 20. Clockwise movement of the steering level rotates the cam wheel 22 to the right. Counterclockwise movement of the steering wheel rotates the cam wheel 22 to the left. Contact between the steering lever 34 and the side of the housing 20 physically limits the range of left and right rotation of the cam wheel 22 within the housing 20.

The steering mechanism 18 also includes an external locking lever 38 that an adhesive couples to the head of the screw 24. The locking lever 38 seats against another 0-ring 36.

Movement of the locking lever 38 rotates the screw 24. Clockwise rotation of the locking lever 38 tightens the screw 24 to increase the seating force between the cam wheel 22 and the bottom washer 28. When moved fully clockwise into contact against the housing 20, the locking lever 38 imposes a seating force that prevents rotation of the cam wheel 22 by the steering lever 34. Counterclockwise movement of the locking lever 34 loosens the screw 24 to decrease the seating force and free the cam wheel 22 for rotation.

The cam wheel 22 includes a forward cam face 40 and a rear cam face 42. The forward cam face 40 is oriented toward the front of the housing 20, where the guide tube assembly 14 attaches. The forward cam face includes a right side surface 44 and a left side surface 46.

The rear cam face 42 is oriented toward the back of the housing 20, where a coaxial cable 48 attaches. The rear cam face includes right and left side surfaces 50 and 52.

The cam wheel 22 also carries a wire fastener 54 between the right and left side surfaces 50 and 52 of the rear cam face 42. The wire fastener 54 holds the proximal ends of right and left catheter steering wires 56 and 58, which are soldered to the interior of the fastener 54.

The steering wires 56 and 58 extend from the opposite ends of the fastener 54 and along the associated left and right side surfaces 44/46 and 50/52 of the front and rear cam faces 40 and 42. The steering wires exit the front of the housing 20 through the interior bore of a tension screw assembly 60.

As will be described in greater detail later, the distal ends of the steering wires 56 and 58 are attached to the electrode tip assembly 16. They extend from the wire fastener 54 through the guide tube assembly 14 to the electrode tip assembly 16.

As also will be described in greater detail, the wire fastener 54 in association with the cam faces 40 and 42 translate rotation of the cam wheel 22 into lateral pulling movement of the steering wires 56 and 58 attached to the electrode tip assembly 16.

By rotating the cam wheel 22 to the left (by moving the steering lever 34 counterclockwise), the left steering wire 58 bears against the left front and rear cam surfaces 46 and 52. The cam surfaces 46 and 52 tension the left steering wire 58 to impose a discrete, constant pulling force that causes the electrode tip assembly 16 to bend to the left.

Also, by rotating the cam wheel 22 to the right (by moving the steering lever 34 clockwise), the right steering wire 56 bears against the right front and rear cam surfaces 44 and 56. The cam surfaces 44 and 56 tension the right steering wire 56 to impose a discrete, constant pulling force that causes the electrode tip assembly 16 to bend to the right.

Rotation of the tension screw assembly 60 additionally varies the amount of slack (i.e., tension) in the steering wires 56 and 58 between the wire fastener 54 and the distal ends of the steering wires 56 and 58. This controls the responsiveness of the electrode tip assembly 16 to rotation of the cam wheel 22.

The component parts of the handle assembly 12 can be constructed of various materials, depending upon the durability needed and the sterilization process used.

For example, when EtO sterilization is used, the housing 20 and bottom washer 28 can be made of a polycarbonate material. In this arrangement, the cam wheel 22, steering lever 34, and locking lever 38 can be made of a delrin material. These plastic materials are durable and EtO sterilizable. In this assembly, the lock nut 30, pin 32, and screw 24 are preferably made of a metallic material like brass or stainless steel.

Figures 3A, 4:
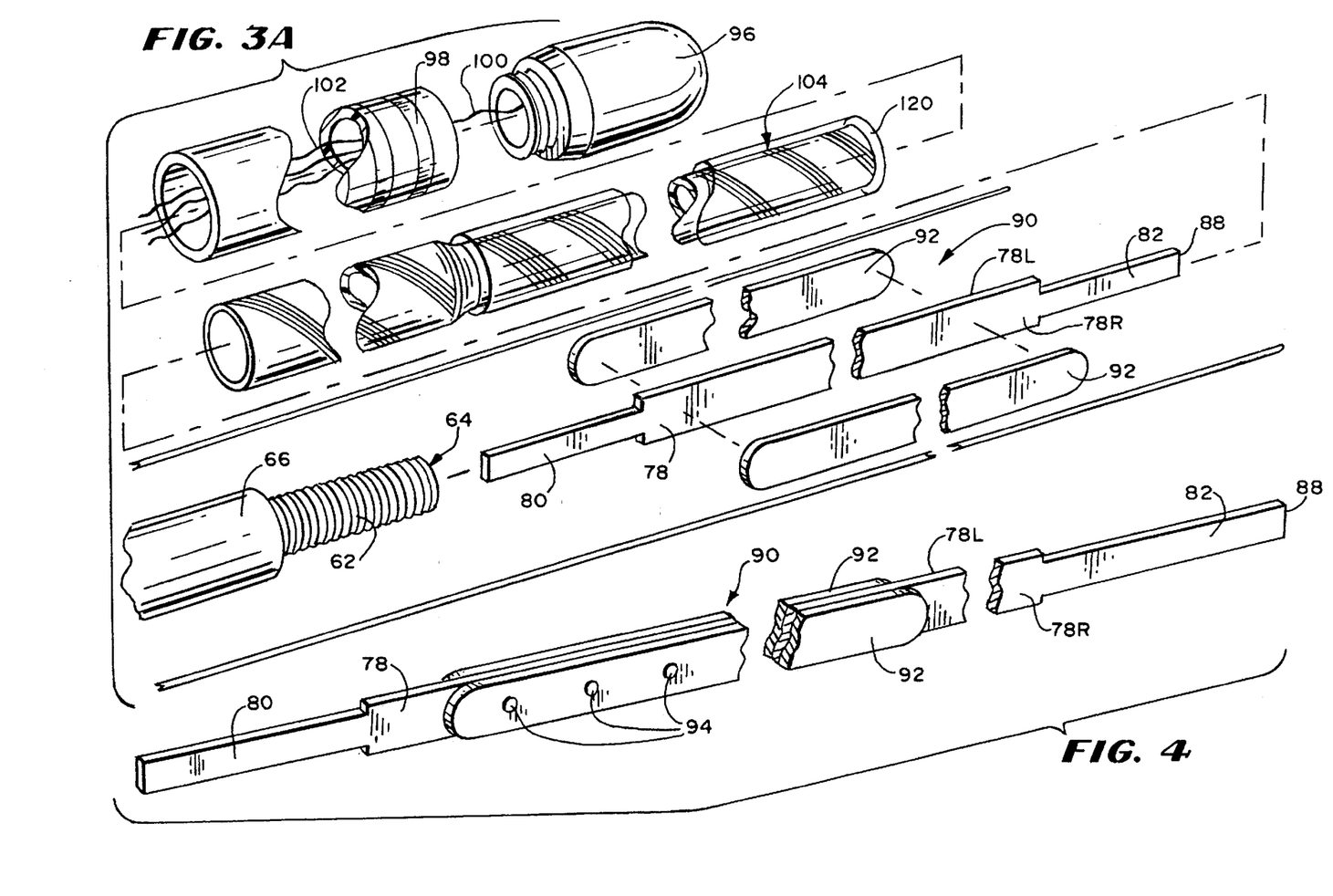
FIG. 3A is an exploded view of the electrode tip assembly of the catheter.
FIG. 4 is a perspective view of the stiffening assembly for the support wire of the catheter.

As FIG. 3A shows, the guide tube assembly 14 includes a flexible shaft 62 attached to the handle assembly 12. The flexible shaft 62 encloses an interior bore 64. The steering wires 56 and 58 pass through the interior bore 64.

The shaft 62 may constructed in various ways. In the embodiment shown in FIG. 3, the shaft 62 comprises a length of stainless steel coiled into a flexible spring enclosing the interior bore 64. A braided sheath 66 of plastic material encloses the coil.

Figure 3B:
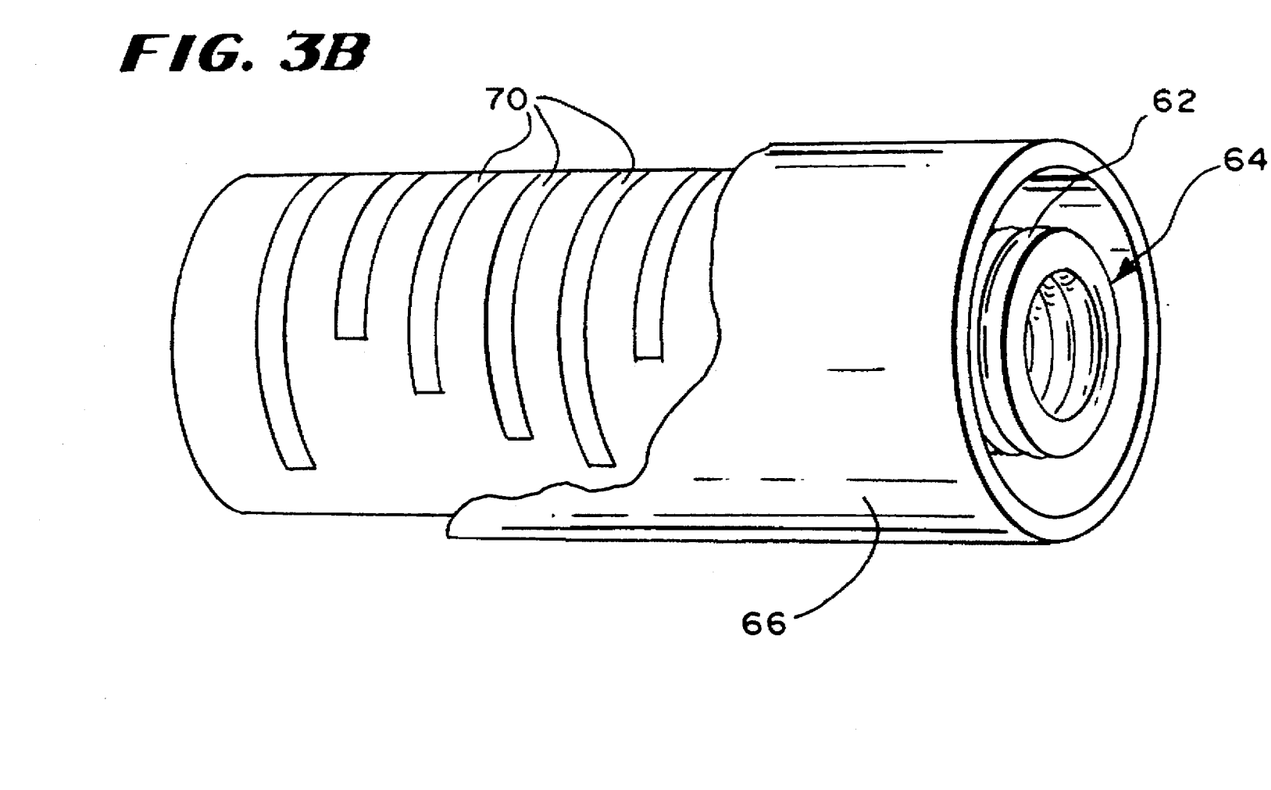
FIG. 3B is a view of an alternative guide tube shaft for the catheter.

Alternatively (as FIG. 3B shows), the shaft 62 comprises a slotted, stainless steel tube enclosing the interior bore 64. An array of slots 70 subtends the tube along its length. The slots 70 subtend less than one circumference of the shaft 62 at an angle of between 270 to 300 degrees. The slots 70 are also radially offset one from the other by about 30 to 120 degrees.

The slotted shaft 62 shown in FIG. 3B provides strength and flexibility along the length of the guide tube assembly 14. The slotted shaft 62 also transmits twisting motions (torque) from the handle assembly 12 to the electrode tip assembly 16 more directly than the coiled shaft 62 shown in FIG. 3. Further details of the slotted shaft 62 are disclosed in pending Lundquist U.S. patent application Ser. No. 07/657,106 filed Feb. 15, 1991, now abandoned and entitled "Torquable Catheter 10 and Method."

Like the coiled shaft 62 in FIG. 3A, a sheath 66 encloses the slotted shaft. The sheath 66 is made from a plastic material, such as polyolefin.

The handle assembly 12 includes a tubular stem 74 though which the proximal end of the guide tube assembly 14 extends for attachment to the tension screw assembly 60. Adhesive attaches the proximal end of the coil to the tension screw assembly 60.

The guide tube assembly 14 can be made in various lengths. In the illustrated, the guide tube assembly 14 is about 100 cm in length.

As FIGS. 1 and 2A/B show, a sleeve 76 couples the guide tube assembly 14 to the handle assembly 12. Adhesive secures one end of the sleeve 76 to the handle stem 74. The sleeve 76 includes an interior bore that progressively tapers from the handle stem 74 into a tight interference fit about the sheath 66 of the guide tube assembly 14. The exterior of the sleeve 76 also tapers, extending about 4 to 5 inches beyond the front of the handle housing 20.

The sleeve 76 is made of a material having a high coefficient of friction, like Krayton G2703. The sleeve 76 provides a gripping surface to help the user manipulate the catheter 10. When used in association with the slotted tube, the sleeve 76 also significantly enhances the transmission of torque from the handle assembly 12 to the electrode tip assembly 16 through the guide tube assembly 14.

The electrode tip assembly 16 includes a bendable main support wire 78 having left and right faces 78L and 78R. In the illustrated embodiment, the main support wire 78 is made of stainless steel flat wire stock in an elongated shape about 0.035 inch wide and about 0.005 inch thick. The main support wire 78 is about 3 inches in total length.

The opposite ends of the main support wire 78 are cut away to form stepped shoulders 80 and 82. In the illustrated embodiment, the shoulders 80 and 82 are about 0.024 inch wide and aligned along the centerline of the main support wire 78. Each shoulder 80 and 82 is about 0.12 inch in length.

As FIG. 3A shows, one stepped shoulder 80 fits within the distal end of the flexible guide tube shaft 62 to append the electrode tip assembly 16 to the guide tube assembly 14. When properly oriented, the left and right faces 78L and 78R of the main support wire 78 lie in a plane that is generally parallel to the axis about which the cam wheel 22 rotates. Stated differently, when the user holds the handle assembly 12 in a horizontal plane, the left and right faces 78L and 78R of the main support wire 78 lie in a vertical plane.

As FIG. 3A shows, the distal end of the left steering wire 58 is soldered to the left face 78L of the main support wire 78. When pulled by left rotation of the cam wheel 22, the left steering wire 58 bends the main support wire 78 to the left.

Also, the distal end of the right steering wire 56 is soldered to the right face 78R of the main support wire 78. When pulled by right rotation of the cam wheel 22, the right steering wire 56 bends the main support wire 78 to the right.

In the illustrated embodiment, the stiffness of the main support wire 78 is not uniform, but varies along its length. Its stiffest point is near its proximal end region, where it joins the guide tube shaft 62. Its stiffness is least at the tip end 88 of the shoulder 82. By varying the stiffness of the main support wire 78 between its proximal end and its distal tip end 88, the base of the electrode tip assembly 16 (where it joins the guide tube assembly 14) resists bending and buckling. The bending forces generated by the steering wires 56 and 58 are directed toward the distal tip end 88 of the main support wire 78. The variable stiffness of the main support wire 78 concentrates the bending forces at the distal tip end 88 of the electrode tip assembly 16.

There are various ways to varying the stiffness of the main support wire 78 along its length. One way (not shown) is to vary the thickness of the main support wire 78 as it is manufactured, so that it is thickest (i.e., most stiff) near the shoulder 80 that, in use, is fitted within the guide tube shaft 62.

In the illustrated and preferred embodiment (see FIG. 4), a stiffening spring assembly 90 stiffens the center support near the distal end of the guide tube shaft 62. The stiffening spring assembly 90 includes two leaf springs 92 that sandwich the main support wire 78 between them. Each leaf spring 92 is made of stainless steel flat wire stock in an elongated shape that is about 0.039 inch wide and about 0.0029 inch thick.

The stiffening spring assembly 90 can sized and configured to provide the degrees of stiffness and variance wanted. In the illustrated embodiment, the stiffening spring assembly 90 stiffens the main support wire 78 beginning about 0.030 to 0.050 inch from the inner edge of the attachment shoulder 80 and extending from there about 1.5 inches.

In the illustrated embodiment, spot welds 94 secure the leaf springs 92 to the main support wire 78. The three spot welds 94 shown are clustered near the proximal end of the stiffening spring assembly 90. There, they are evenly spaced, with the most distal spot weld 94 being about 0.10 inch from the proximal end of the stiffening spring assembly 90.

In the illustrated embodiment, the distal end of the electrode tip assembly 16 carries an ablation tip electrode 96 and three ring electrodes 98. Interior conducting wires 100 are connected to the tip electrode 96 and the three ring electrodes 98. The conducting wires 100 extend along the main support wire 78, through the interior bore of the guide tube shaft 62, and into the handle housing 20 to join the coaxial cable 48 that extends from the rear of the housing 20.

The coaxial cable 48 ends with plugs 102. The plugs 102 connect with appropriate conventional catheter control equipment (not shown). The conducting wires 100 transfer electrical current from the ring electrodes 98 indicative of electrical activity within the heart. The conducting wires 100 also transfer radio frequency energy to the tip electrode 96 to carry out ablation procedures within the heart.

There are various ways of securing the attachment between the electrode tip assembly 16 and the guide tube assembly 14. The illustrated embodiment employs a reinforcing sleeve assembly 104 for this purpose.

Figure 5A:
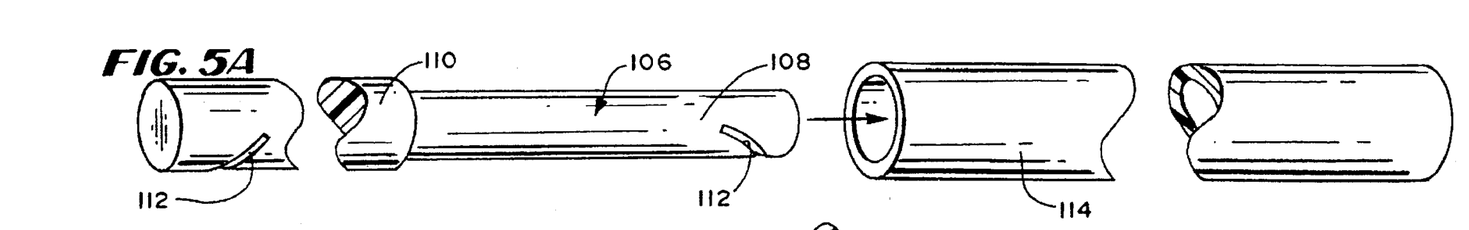
FIGS. 5A to D show the assembly of reinforcing tube that surrounds the support wire of the catheter.

As shown in the FIGS. 5A to D, the reinforcing sleeve assembly 104 is made in association with a specially designed sleeve mandrel 106. In the illustrated embodiment, the sleeve mandrel 106 is made from stainless steel and is about 7 inches in total length. As FIG. 5A shows, the mandrel 106 has a first cylindrical body portion 108 and second cylindrical body portion 110 having an enlarged diameter. In the illustrated embodiment, the first body portion 108 is about 0.032 inch in diameter and is about 5 inches long. The second body portion 110 has an enlarged diameter of about 0.043 inch and is about 2 inches long. The first body portion 108 and the second body portion 110 each includes an inwardly sloping notch 112.

In making the reinforcing sleeve assembly 104 (see FIG. 5A), a sleeve mandrel 106 receives a first heat shrink tube 114 that, in the illustrated embodiment, is about 4.5 inches long. A portion of the first tube 114 is pulled over the second body portion 110 of the mandrel 106. Heat is applied using an oven or heat gun to shrink the tube in place upon the sleeve mandrel 106.

Next (see FIG. 5B), a reinforcing fabric 116 is wrapped in tension over the first tube 114 while still on the mandrel 106. The fabric 116 is wrapped as a single spiral about the first tube 114 to obtain a desired, closely spaced pitch. In the illustrated embodiment the fabric 116 is wrapped to a pitch of about 18 to 20 wraps per inch. The notches 112 on the sleeve mandrel 106 hold the fabric 116 in tension during this step of the manufacturing process.

Figures 5B, 5C:
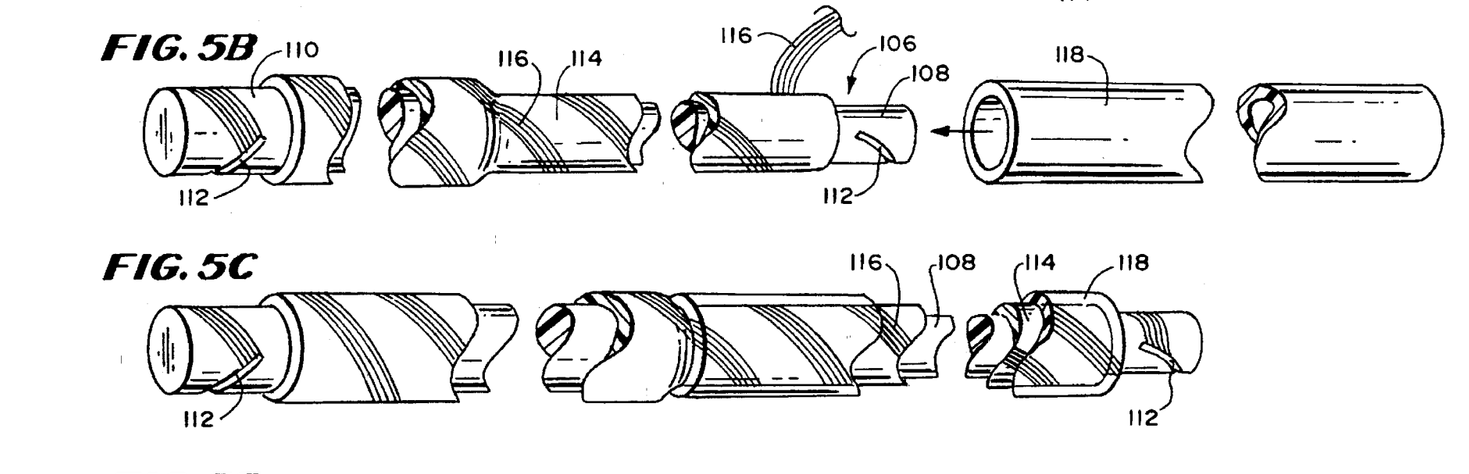
Figure 5D:
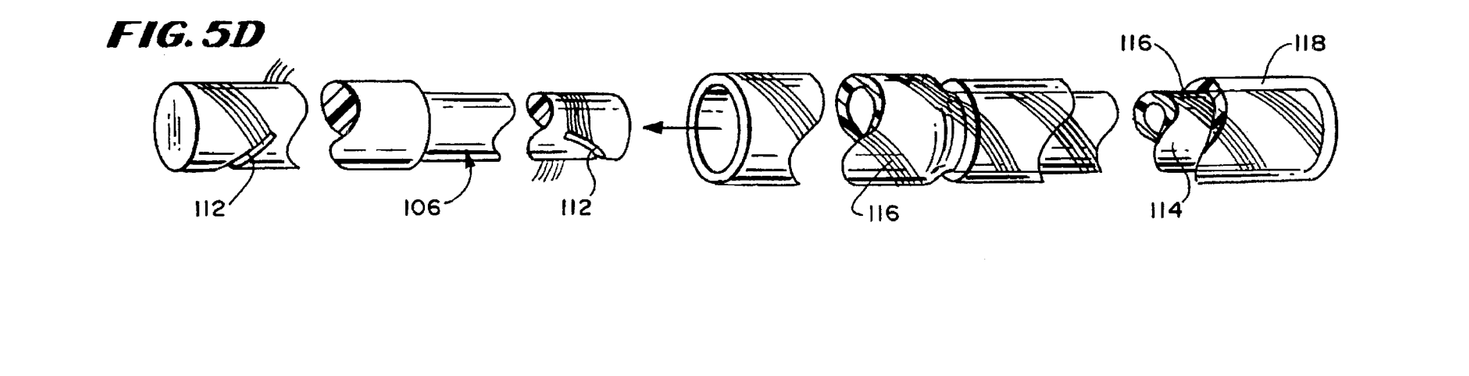

The mandrel 106 now receives a second heat shrink tube 118 over the fabric-wrapped first tube 114 (see FIGS. 5B and 5C). The second tube 118 is shorter than the first tube 114, and is not pulled over the second body portion 110 of the sleeve mandrel 106. In the illustrated embodiment, the second tube 118 is about 4.0 inches long.

Heat is again applied using an oven or heat gun to shrink the second tube 118 in place over the fabric-wrapped first tube 114. When shrunk in place, the second tube 118 captures and encases the wrapped fabric 116 and underlying first tube 114 (as FIG. 5C shows).

Next (see FIG. 5D), the fabric 116 extending from the second tube 118 to the notches 112 is cut away. The reinforcing sleeve assembly 104 is removed from mandrel 106.

The reinforcing sleeve assembly 104 is inserted over the main support wire 78 appended to the distal end of the guide shaft 62 (see FIG. 3A) so that the enlarged diameter portion of the reinforcing sleeve assembly 104 slips over the distal end of the guide shaft 62. At this time, the left and right steering wires 56 and 58 and stiffening spring assembly 90 are attached to the main support wire 78. The conducting wires 100 also extend along the main support wire 78 and into the bore of the guide shaft 62.

Heat is again applied using an oven or heat gun to finally shrink the second tube 118 in place over distal end of the guide shaft 62 and over the main support wire 78 and its associated parts. When finally shrunk in place, the reinforcing sleeve assembly 104 tightly encases the main support wire 78.

The wrapped fabric 116 becomes an integrated part of the reinforcing sleeve assembly 104. The reinforcing sleeve assembly 104 is flexible enough to accommodate the bending movement desired for the electrode tip assembly 16. Still, due to the wrapped fabric 116, the reinforcing sleeve assembly 10 provides added strength and resistance against wear and tear during repeated bending operations.

The reinforcing sleeve assembly 104 also holds the steering wires 56 and 58 and conducting wires 100 in close intimate contact against the main support wire 78. The intimate contact prevents kinking and chafing of the steering wires 56 and 58 and conducting wires 100 during bending operations.

The materials used to make the reinforcing sleeve assembly 104 can vary. In the illustrated embodiment, the shrink tubes 114 and 118 are made from medical grade TFE Teflon material having a 2 to 1 shrink ratio. The material used has a wall thickness (after heat shrinkage) of about 0.003 to 0.0045 inch. In the illustrated embodiment, the fabric 116 is a KEVLAR 49 Yarn (which is available from DuPont). This material has a tensile strength of about 400,000 lbs/in$^2$ and a modulus of about 18,000,000 lbs/in$^2$.

An outer tube 120 covers the reinforcing sleeve assembly 104. The tip electrode 96 and ring electrodes 98 are attached to the conducting wires 100 and joined to the outer tube 120 by conventional methods to complete the electrode tip assembly 16.

Figure 11:
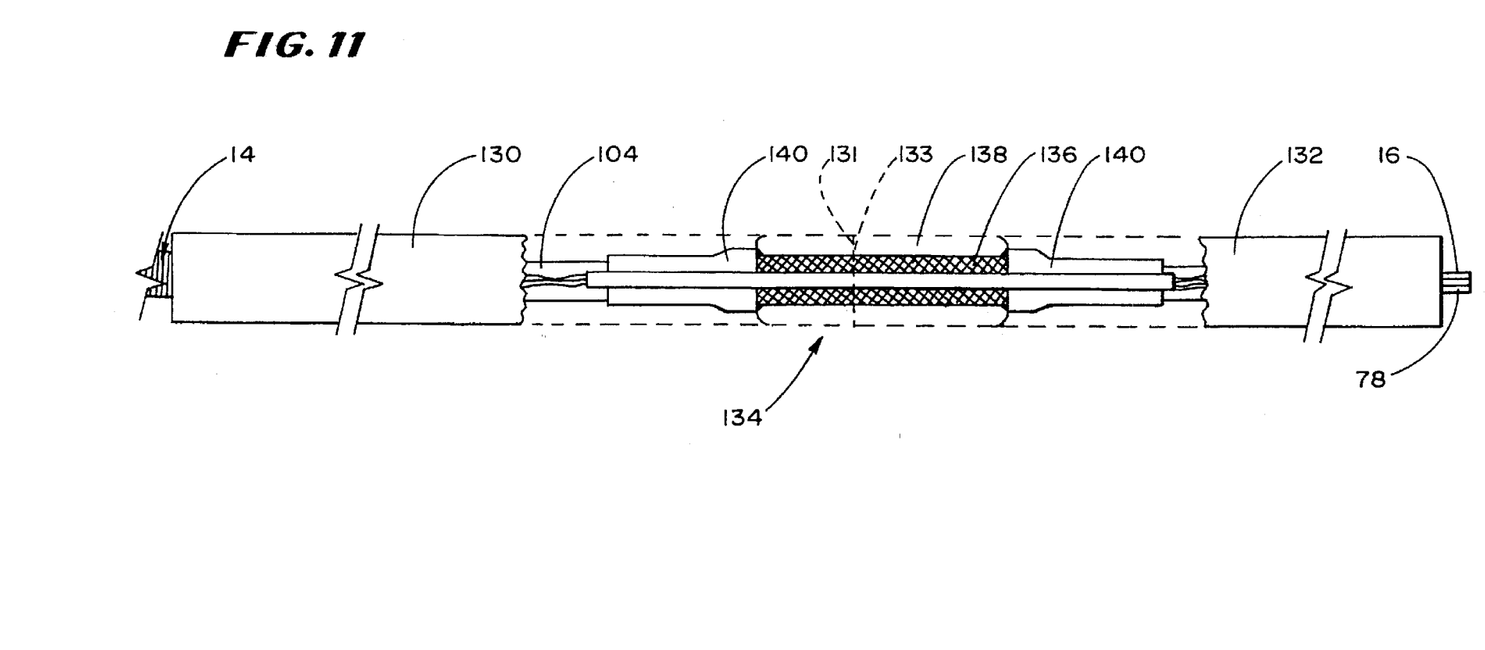
FIG. 11 is a cut away interior side view of the flexible bond that joins the exterior sleeve of the guide tube assembly to the exterior sleeve of the electrode tip assembly.

FIG. 11 shows an alternative embodiment for the junction between the electrode tip assembly 16 and the guide tube assembly 14. In this arrangement, a first outer sleeve 130 encloses the guide tube assembly 14, while a second outer sleeve 132 encloses the electrode tip assembly 16.

The first outer sleeve 130 is made of a material that is selected to best transmit twisting motions (torque) along the guide tube assembly 14 to the electrode tip assembly 16.

The second outer sleeve 132 is made of a material that is selected to best accommodate the side to side flexing of the electrode tip assembly 16 relative to the guide tube assembly 14.

By using sleeves 130 and 132 having different physical characteristics, the different individual functions of the guide tube assembly 14 and the electrode tip assembly 16 can be best achieved.

The materials selected can vary. In the illustrated and preferred embodiment, the first outer sleeve 130 comprises a durable, braided material. The second outer sleeve 132 comprises a durable, flexible material, like urethane.

As FIG. 11 shows, the terminal ends 131 and 133 of the first and second outer sleeves 130 and 132 abut about the reinforcing sleeve assembly 104. An adhesive butt bond can be used to join the sleeve ends 131 and 133 together.

According to this aspect of the invention, a flexible junction 134 joins the sleeve 130 and 132. The flexible junction 134 holds the two sleeves 130 and 132 securely together in fluid tight abutment, preventing their axial separation during use. The flexible junction 134 also allows the electrode tip assembly 16 to flex freely at the end of the guide tube assembly 14 without stretching the abutting sleeve ends 131 and 133 apart. The flexible junction 134 further transmits torque from the guide tube assembly 14 to the electrode tip assembly 16 without twisting the abutting sleeve ends 131 and 133 apart. The flexible junction prevents fluid from invading the interior regions of the guide tube and electrode tip assemblies 14 and 16 during use.

The flexible junction 134 comprises an inner sleeve 136 that underlies the terminal ends 131 and 133 of the outer sleeves 130 and 132. The inner sleeve 136 is secured about the main support wire 78 appended to the distal end of the guide shaft 62. An adhesive material 138 occupies the space between the inner sleeve and the overlying portions of the outer sleeves 130 and 132. The adhesive material 138 secures the outer sleeves 130 and 132 to the inner sleeve 136.

In the illustrated and preferred embodiment, the inner sleeve 136 encircles a portion of the reinforcing sleeve assembly 104. The inner sleeve 136 is made of a flexible material that has a tensile strength greater than the outer sleeves 130 and 132. A non-rigid metal material like 304 Stainless Steel Mesh can be used. Alternatively, a woven non-rigid fabric material like Kevlar 49 Yarn can be used. Alteratively, a non-rigid thermal plastic material can be used. The material selected depends upon the tensile strength and degree of flexibility desired.

Oppositely spaced collars 140 secure the inner sleeve 136 to the reinforcing sleeve assembly 104. Adhesive can be used to hold the collars 140 in place. However, in the illustrated and preferred embodiment, the collars 140 are made of a heat shrink material, like TFE Teflon.

In this arrangement, the inner sleeve 136 is fitted to the sleeve assembly 104 (as FIGS. 12A and B show), either by wrapping or by sliding into place. As FIG. 12A shows, the region 142 of the sleeve assembly 104 that the sleeve 136 overlies can be chemically etched or otherwise roughened to increase the surface friction between the two.

Figure 12:
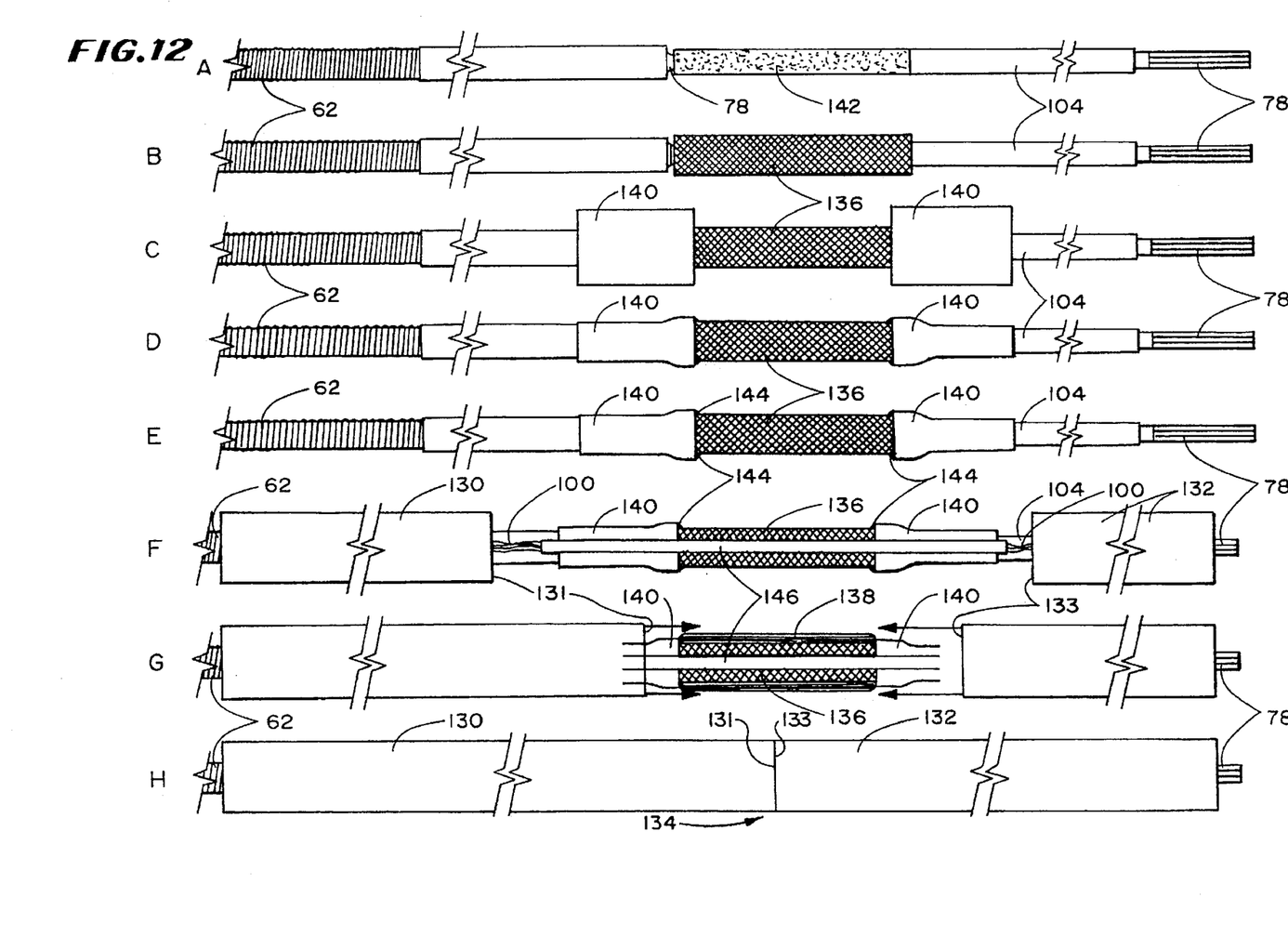
FIG. 12A to H show the assembly of flexible bond shown in FIG. 11.

As FIG. 12C shows, the collars 140 are next fitted at opposite ends of the sleeve 136. As FIG. 12D shows, heat is applied using an oven or heat gun to shrink the collars 140 about the ends of the sleeve 136.

As FIG. 12E shows, adhesive 144 is applied to seal the inner edge of the collars 140 to the sleeve 136.

The collars 140 serve not only to secure the sleeve 136 about the main support wire 78, but they also serve as dams to retain adhesive and prevent its leakage beyond the ends of the sleeve 136.

In the illustrated and preferred embodiment see FIG. 12F), a flexible conduit 146 (for example, one made from TFE Teflon material) axially overlies the sleeve 136. The ends of the conduit 146 extend beyond the collars 140. The electrical conducting wires 100 associated with the electrode tip assembly 16 pass through the conduit 146. The conduit 146 protects the wires 100 from the influx of adhesive material 138.

As FIG. 12F shows, the outer sleeves 130 and 132 are next fitted to the guide tube assembly 14 and electrode tip assembly 16. The terminal ends 131 and 133 are positioned on opposite sides of the secured sleeve 136.

The adhesive material 138 is applied to the sleeve 136 (and overlying conduit 146) between the collars 140 (as FIG. 12G shows). Next, the terminal sleeve ends 131 and 133 are brought into abutment over the adhesive material 138, completing the assembly (as FIG. 12H shows). Optionally, a sleeve 148 (shown in phantom lines in FIG. 12H) can be fitted about the junction 134 to cover the abutting sleeve ends 131 and 133.

The adhesive material 138 is a heat sterilizable, rapid cure adhesive, like cyanoacrylate. If greater flexibility is desired at the junction 134, a urethane adhesive can be used.

As can be seen, the flexibility of the junction 134 can be tailored to the specific application by the selection of material for the sleeve 136 and choice of adhesive material 138.

In the illustrated embodiment, the curvature assumed upon bending the electrode tip assembly 16 to the left is different that the curvature assumed upon bending the electrode tip assembly 16 to the right. The electrode tip assembly 16 assumes one curvature when bent to the left and a different curvature when bent to the right. These different left and right curvatures provide the physician with flexibility in steering the tip electrode 96 into position. These differing curvatures will be called asymmetric curves.

The drawings show five representative asymmetric curve options that embody the features of the invention. The invention achieves the different curve options by varying two relationships.

The first relationship is that between the cam radius on the left side surfaces 46 and 52 of the forward cam and rear cam faces 40 and 42, and the cam radius on the right side surfaces 44 and 50 of the forward and rear cam faces 40 and 42. According to the invention, the cam radii differ, forming various asymmetric cam arrangements.

The second relationship is that between the point of attachment of the left steering wire 58 on the left face 78L of the main support wire 78 and the point of attachment of the right steering wire 56 on the right face 78R of the main support wire 78. According to the invention, the point of attachment can be varied, forming both symmetrical and asymmetric steering wire attachment sites.

Combinations of asymmetric cam arrangements and symmetrical and asymmetric steering wire attachments create differing asymmetric curve options. The five curve options shown are intended to illustrate the ideas of forming asymmetric curves by varying the two relationships, but they do not encompass all the possible curve options that can be made.

Asymmetric Curve Option 1

Figures 6A, 6B:
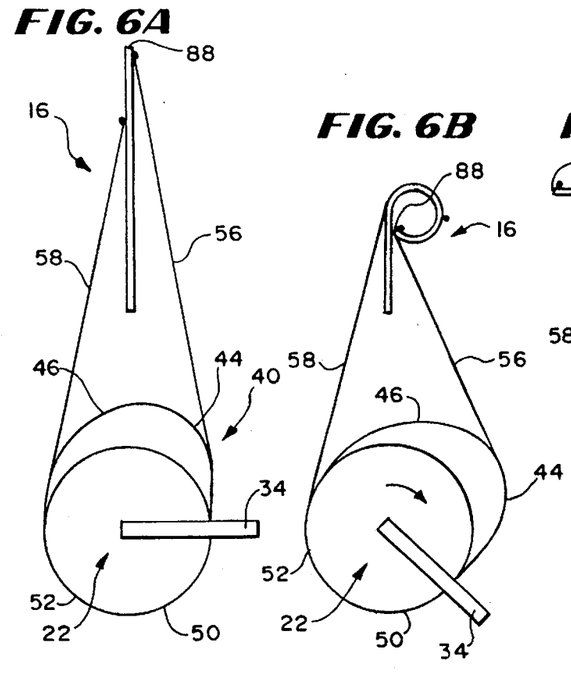
FIGS. 6A to C show the steering mechanism for Curve Option 1 of the catheter.
Figure 6C:
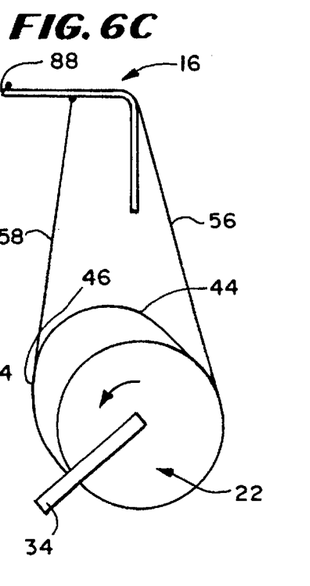

As FIGS. 6A to C show, the catheter 10 includes an asymmetric forward cam face 40 on the cam wheel 22 and a symmetrical rear cam face 42. In addition, the electrode tip assembly 16 includes asymmetric attachments of the left and right steering wires 56 and 58 to the left and right faces 78L and 78R of the main support wire 78.

More particularly, the right side surface 44 of the forward cam face 40 is formed with a radius of 0.3125 inch, while the left side surface 46 of the forward cam face 40 is formed with a radius of 0.4062 inch. The right and left side surfaces 50 and 52 of the rear cam face 42 each has a radius of 0.313".

The right steering wire 56 is attached at the distal tip 88 of the main support wire 78, while the left steering wire 58 is attached about 1.5 inches from the distal tip 88 of the main support wire 78.

When the steering lever 34 is rotated clockwise, the foregoing relationships bend the main support wire 78 about 270 degrees to the right to form a looping "pigtail" curve. When the steering lever 34 is rotated counterclockwise, the foregoing relationships bend the main support wire 78 about 90 degrees to the left to form an elbow curve.

Asymmetric Curve Option 2

Figure 7A:
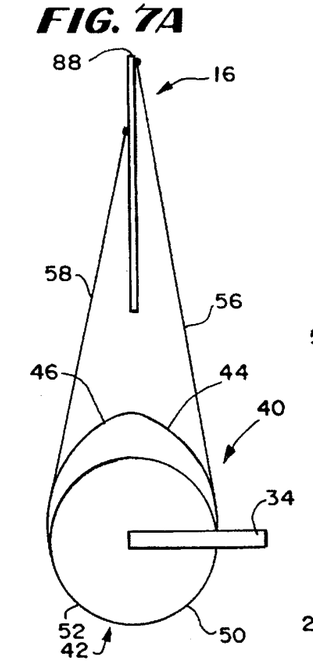
FIGS. 7A to C show the steering mechanism for Curve Option 2 of the catheter.
Figures 7B, 7C:
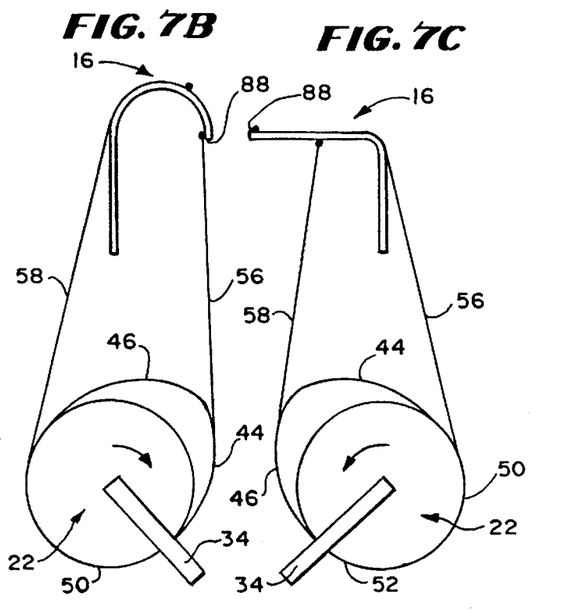

As FIGS. 7A to C show, the catheter 10 includes symmetrical forward and rear cam faces 40 and 42 on the cam wheel 22 in combination an asymmetric attachment of the left and right steering wires 56 and 58 to the main support wire 78 to achieve the asymmetric left and right curves in Option 2.

More particularly, the right side surface 44 and the left side surface 46 of the forward cam face 40 are both formed with a radius of 0.4062 inch. The right side surface 50 and the left side surface 52 of the rear cam face 42 are both formed with a radius of 0.313".

The right steering wire 56 is attached at the distal tip 88 of the main support wire 78, while the left steering wire 58 is attached about 1.5 inches from the distal tip of the main support wire 78.

When the steering lever 34 is rotated clockwise, the foregoing relationships bend the main support wire 78 about 135 degrees to the right to form an open, arching curve. When the steering lever 34 is rotated counterclockwise, the foregoing relationships bend the main support wire 78 about 90 degrees to the left to form an elbow curve (just as in Curve Option 1).

Asymmetric Curve Option 3

Figure 8A:
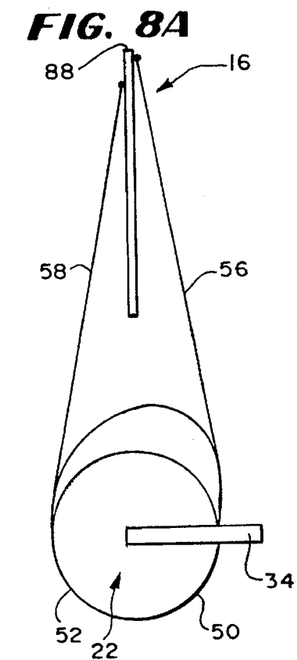
FIGS. 8A to C show the steering mechanism for Curve Option 3 of the catheter.
Figures 8B, 8C:
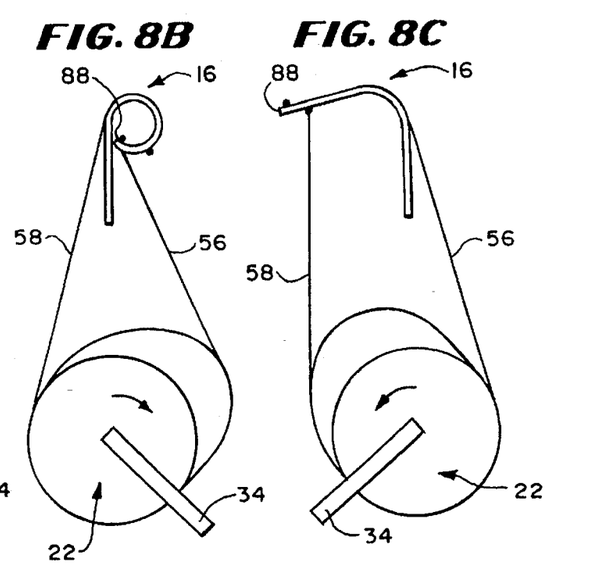

As FIGS. 8A to C show, the catheter 10 includes an asymmetric forward cam face 40 on the cam wheel 22 and a symmetrical rear cam face 42. In addition, the electrode tip assembly 16 includes symmetrical attachments of the left and right steering wires 56 and 58 to the left and right faces 78L and 78R of the main support wire 78.

More particularly, the right side surface 44 of the forward cam face 40 is formed with a radius of 0.3125 inch, while the left side surface 46 of the forward cam face 40 is formed with a radius of 0.4062inch. The right and left side surfaces 50 and 52 of the rear cam face 42 each has a radius of 0.313".

The right and left steering wires 56 and 58 are attached at the distal tip 88 of the main support wire 78.

When the steering lever 34 is rotated clockwise, the foregoing relationships bend the main support wire 78 about 270 degrees to the right to form a looping "pigtail" curve (as in Curve Option 1, where the same cam and steering wire relationships exist on the right side). When the steering lever 34 is rotated counterclockwise, the foregoing relationships bend the main support wire 78 about 80 degrees to the left to form a partial arch.

Asymmetric Curve Option 4

Figure 9A:
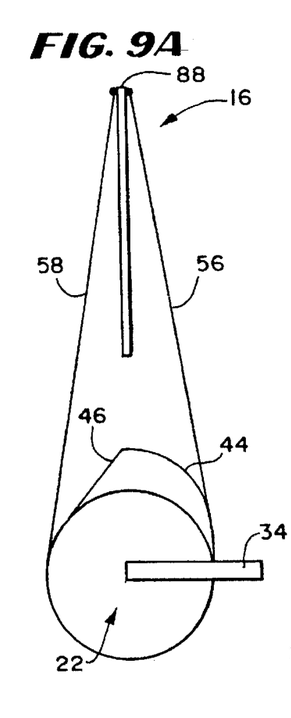
FIGS. 9A to C show the steering mechanism for Curve Option 4 of the catheter.
Figures 9B, 9C:
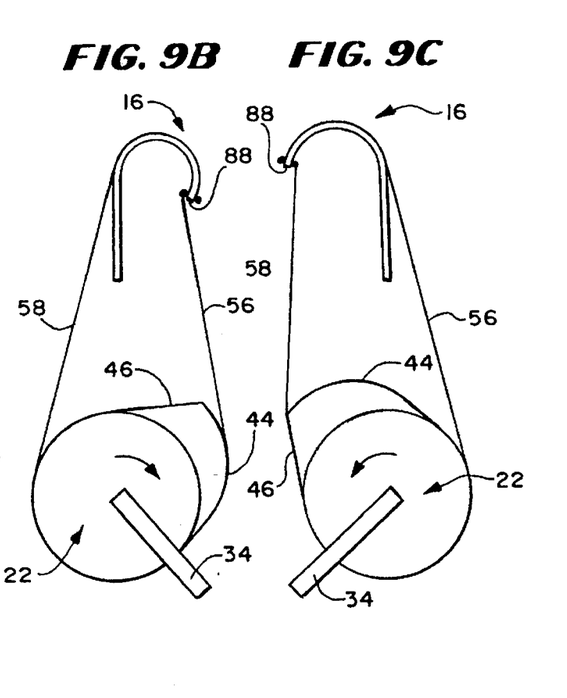

As FIGS. 9A to C show, both forward and rear cam faces 40 and 42 on the cam wheel 22 are asymmetric. The electrode tip assembly 16 includes a symmetrical attachment of the left and right steering wires 56 and 58 to the main support wire 78.

More particularly, the right side surface 44 of the forward cam face 40 is formed with a radius of 0.3125 inch. The left side surface 52 of the forward cam face 40 is formed as a straight (i.e., linear) line. The linear line extends along a tangent from an interior hub 68 of the cam wheel 22 to intersect the curved (i.e., nonlinear) right side surface 44.

The left side surface 52 of the rear cam face 42 extends arcuately from the tangent along the circumference of the interior hub 68. In contrast, the right side surface 50 is asymmetrically formed with a radius of 0.313"

The right steering wire 56 and the left steering wire 52 are both attached at the distal tip 88 of the main support wire 78.

When the steering lever 34 is rotated clockwise, the foregoing relationships bend the main support wire 78 in an open arch about 135 degrees. When the steering lever 34 is rotated counterclockwise, the foregoing relationships bend the main support spring in a tighter arch about 135 degrees to the left to form a "shepard's crook" curve.

Asymmetric Curve Option 5

Figure 10A:
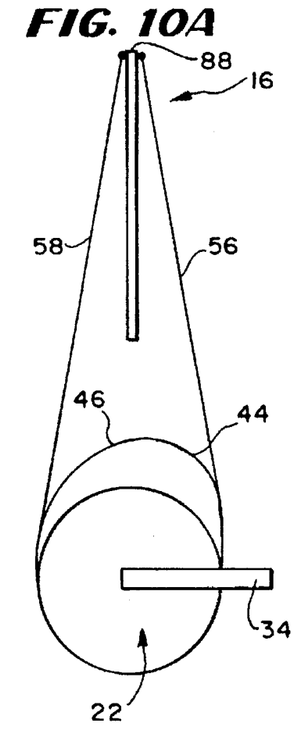
FIGS. 10A to C show the steering mechanism for Curve Option 5 of the catheter.
Figures 10B, 10C:
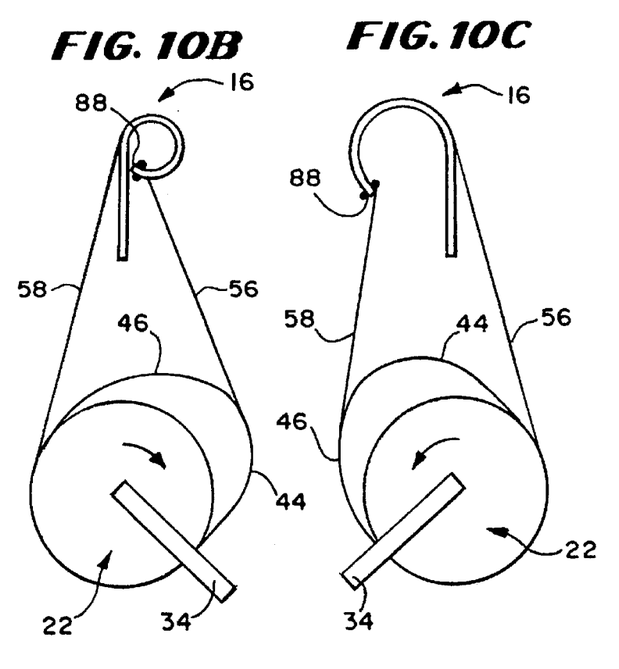

As FIGS. 10A to C show, the catheter 10 includes an asymmetric forward cam face 40 and a symmetrical rear cam face 42. The electrode tip assembly 16 includes symmetrical attachments of the left and right steering wires 56 and 58 to the main support wire 78.

More particularly, the right side surface 50 of the forward cam face 40 is formed with a radius of 0.3125 inch, while the left side surface 46 of the forward cam face 40 is formed with a radius of 0.4062inch. The left and right side surfaces 50 and 52 of the rear cam face 42 are each formed with a radius of 0.313".

The right steering wire 56 and the left steering wire 58 are both attached at the distal tip 88 of the main support wire 78.

When the steering lever 34 is rotated clockwise, the foregoing relationships bend the main support spring about 270 degrees to the right to form the looping "pigtail" curve (as in Curve Options 1 and 3). When the steering lever 34 is rotated counterclockwise, the foregoing relationships bend the main support spring about 135 degrees to the left to form a "shepard's crook" curve (like the right curve in Curve Option 4).

The following table summarizes the relationships that were varied to achieve Curve Options 1 to 5.

TABLE 1

| | Asymmetric Curve Options 1 to 5 | | | |
|---|---|---|---|---|
| Curve Option | Left Wire | Left Cam* | Right Wire | Right Cam* |
| 1 | 1.5" | .4062" | Tip | .3125" |
| 2 | 1.5" | .4062" | Tip | .4062" |
| 3 | 0.75" | .4062" | Tip | .3125" |
| 4 | Tip | Linear | Tip | .4062" |
| 5 | Tip | .4062" | Tip | .3125" |

*Note: These columns refer to the left and right cam surfaces on the front cam face. In Curve Options 1, 2, 3 and 5, the left and right cam surfaces of the rear cam face are symmetrical, having a radius of .313". In Curve Option 4, the left and right cam surfaces of the rear cam are asymmetric, with the right cam surface formed with a radius of .3125 inch and the left cam face being linear (not curved).

Various features of the invention are set forth in the following claims.

We claim:

1. An electrode tip assembly including at least one electrode, the assembly comprising a center support wire that is bendable in response to external forces, a guide tube joined to an end of the center support wire for positioning the center support wire and for holding the center support wire while it bends in response to external forces, an interior sleeve attached to a portion of the center support wire near its junction with the guide tube, a first exterior sleeve enclosing the center support wire and having an end portion overlying the interior sleeve, the first exterior sleeve being sufficiently flexible to conform to the shape of the center support wire while it bends, a second exterior sleeve enclosing the guide tube and having an end portion that extends beyond the end of the guide tube and overlies the interior sleeve, the end portions of the first and second exterior sleeves abutting about the interior sleeve, the second exterior sleeve being operative for transmitting twisting forces along the guide tube toward the center support wire, the interior sleeve having a tensile strength greater than the tensile strength of the first and second exterior sleeves, and means forming a flexible adhesive bond between the interior sleeve and the abutting overlying end portions of the first and second exterior sleeves to hold the end portions in abutment during twisting of the guide tube and bending of the central support wire.

2. An assembly according to claim 1 wherein the interior sleeve is made of a steel mesh material.

3. An assembly according to claim 1 wherein the interior sleeve is made of a non-rigid fabric.

4. An assembly according to claim 1 wherein the means forming its flexible adherent bond is cyanoacrylate.

5. An assembly according to claim 1 wherein the means forming the flexible adhesive bond is a urethane material.

6. An assembly according to claim 1 and further including means forming barriers at opposite ends of the interior sleeve to prevent flow of means forming the flexible adhesive bond beyond the ends of the interior sleeve.

7. An assembly according to claim 1 and further including means defining a conduit for passing an electrical conducting wire through the means forming the flexible adhesive bond free of contact with it.

8. An electrode tip assembly including at least one electrode, the assembly comprising a center support wire that is bendable in response to external forces, and having a proximal end, a guide tube having a distal end joined to the proximal end of the center support wire for positioning the center support wire and for holding the center support wire while it bends in response to external forces, a steering wire extending through the guide tube and attached to the center support wire for applying a bending force, a first flexible tube having an end portion surrounding the distal end of the guide tube and a body portion in intimate contact with the center support wire and the attached steering wire, a second flexible tube surrounding and in intimate contact with the body portion of the first flexible tube, a non-rigid fabric having a tensile strength greater than the first and second flexible tubes sandwiched between the body portion of the first flexible tube and the second flexible tube, an interior sleeve attached about a portion of the second flexible tube near the junction of the center support wire with the guide tube, a first exterior sleeve enclosing the second flexible tube and having an end portion overlying the interior sleeve, the first exterior sleeve being sufficiently flexible to conform to the shape of the center support wire while it bends, a second exterior sleeve enclosing the guide tube and having an end portion that extends beyond the distal end of the guide tube and that overlies the interior sleeve, the end portions of the first and second exterior sleeves abutting about the interior sleeve, the second exterior sleeve being operative for transmitting twisting forces along the guide tube toward the center support wire, the interior sleeve having a tensile strength greater than the tensile strength of the first and second exterior sleeves, and means forming a flexible adhesive bond between the interior sleeve and the abutting overlying end portions of the first and second exterior sleeves to hold the end portions in abutment during twisting of the guide tube and bending of the central support wire.

9. An assembly according to claim 8 wherein the interior sleeve is made of a steel mesh material.

10. An assembly according to claim 8 wherein the interior sleeve is made of a non-rigid fabric.

11. An assembly according to claim 8 wherein the means forming the flexible adhesive bond is cyanoacrylate.

12. An assembly according to claim 8 wherein the means forming the flexible adhesive bond is a urethane material.

13. An assembly according to claim 8 and further including means forming barriers at opposite ends of the interior sleeve to prevent flow of means forming the flexible adhesive bond beyond the ends of the interior sleeve.

14. An assembly according to claim 8 and further including means defining a conduit for passing an electrical conducting wire through the means forming the flexible adhesive bond free of contact with it.

* * * * *